US008887595B2

(12) United States Patent
Williams (10) Patent No.: US 8,887,595 B2
(45) Date of Patent: Nov. 18, 2014

(54) INSTRUMENT WRIST WITH CYCLOIDAL SURFACES

(75) Inventor: Matthew R. Williams, Walnut Creek, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 942 days.

(21) Appl. No.: 12/645,391

(22) Filed: Dec. 22, 2009

(65) Prior Publication Data

US 2011/0152879 A1   Jun. 23, 2011

(51) Int. Cl.
*B25J 17/00* (2006.01)
*A61B 19/00* (2006.01)
*A61B 17/00* (2006.01)

(52) U.S. Cl.
CPC ....... *A61B 19/2203* (2013.01); *A61B 2017/003* (2013.01); *A61B 2017/00314* (2013.01); *A61B 2017/00327* (2013.01); *A61B 2019/2226* (2013.01); *A61B 2019/2242* (2013.01); *A61B 2019/2238* (2013.01); *Y10S 901/28* (2013.01)
USPC .............................. 74/490.05; 606/1; 901/28

(58) Field of Classification Search
USPC ................. 74/457, 462, 465, 490.04, 490.05; 600/142; 606/1; 16/221, 242, 354; 384/2–6; 623/20.22
See application file for complete search history.

(56) References Cited

U.S. PATENT DOCUMENTS

| | | | | |
|---|---|---|---|---|
| 1,976,458 A * | 10/1934 | Olsen | | 24/33 M |
| 3,132,911 A * | 5/1964 | Heidler | | 439/31 |
| 3,324,683 A | 6/1967 | Schroter | | |
| 3,747,368 A | 7/1973 | Morin | | |
| 4,224,696 A * | 9/1980 | Murray et al. | | 623/20.29 |
| 4,922,781 A * | 5/1990 | Peiji | | 74/462 |
| 6,023,989 A * | 2/2000 | Imase et al. | | 74/422 |
| 6,817,974 B2 | 11/2004 | Cooper et al. | | |
| 2008/0065102 A1 | 3/2008 | Cooper | | |
| 2010/0116080 A1 | 5/2010 | Pistor et al. | | |
| 2010/0116081 A1 | 5/2010 | Pistor et al. | | |
| 2011/0079098 A1* | 4/2011 | Nowicki | | 74/411 |

FOREIGN PATENT DOCUMENTS

| | | |
|---|---|---|
| CN | 85106551 A | 4/1987 |
| EP | 0532440 A1 | 3/1993 |
| JP | 2005163593 A | 6/2005 |
| JP | 2007239792 A | 9/2007 |
| JP | 2009160011 A | 7/2009 |
| SU | 719624 A1 | 3/1980 |
| WO | WO03001986 | 1/2003 |

OTHER PUBLICATIONS

Vertut, Jean et al., Robot Technology:Teleoperation and Robotics Evolution and Development, 1986, vol. 3A, 332 pages, English translation, Prentice-Hall, Inc., Inglewood Cliffs, New Jersey, USA.
PCT/US10/59366 International Search Report and Written Opinion of the International Searching Authority, mailed Feb. 17, 2011, 7 pages.

* cited by examiner

*Primary Examiner* — William C Joyce (57) ABSTRACT

An instrument wrist uses members having epicycloidal and hypocycloidal surfaces to bear loads and preserve a separation of reference points in the same manner as circles rolling on each other. The cycloidal surfaces can be uniform, stepped, or blended and can be arranged to ensure geared motion of members without addition of additional gearing structures. A hypocycloidal surface provides a concave contact that improves resistance to deformations under load. The wrist mechanism is tendon stayed, which keeps members in contact, and optionally gear structures can be integrated into the members to ensure geared motion and support roll toques.

27 Claims, 10 Drawing Sheets

FIG. 12

INSTRUMENT WRIST WITH CYCLOIDAL SURFACES

BACKGROUND

Medical instruments for minimally invasive procedures often employ mechanical wrists or joints that are remotely activated. In some configurations, a wrist mechanism may be part of or may manipulate a tool such as forceps, a scalpel, scissors, or a cauterizing tool that is at the distal end of a main tube of the instrument. Tendons generally attach to the mechanical members or disks in the wrist mechanism and extend through the main tube to a drive system at the proximal end of the main tube. U.S. Pat. No. 6,817,974, entitled "Surgical tool having Positively Positionable Tendon-Actuated Multi-Disk Wrist Joint," to Cooper et al. describes some known wrist mechanisms containing multiple disks and tendon controlled wrist joints.

Figure 1A:
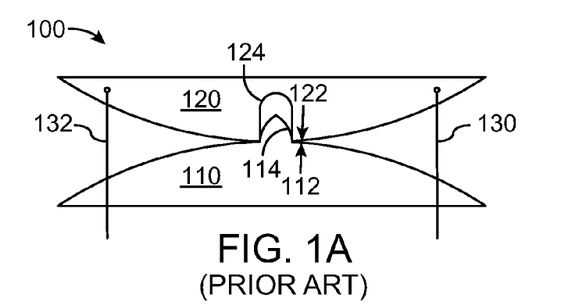
FIGS. 1A and 1B show side views of a known wrist joint that uses a pin and aperture to constrain contacting members to geared motion.
Figure 1B:
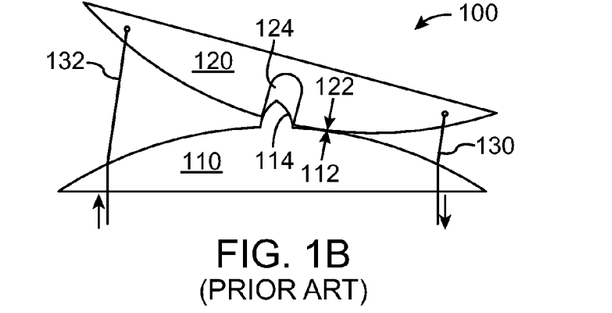

Geared movement in a wrist mechanism results at a joint when two members in the mechanism have relative angular orientations that change according to a fixed relationship or gear ratio. FIG. 1A, for example, shows a side view of a wrist joint 100 having members 110 and 120 with load-bearing surfaces 112 and 122 that are circular and have the same radius of curvature. Geared motion with a 1:1 gear ratio results when circular surfaces 112 and 122 roll on each other without slipping. To prevent slipping, a pin or tooth 114 on member 110 can engage the walls of an aperture 124 in member 120, and prevent members 110 and 120 from slipping relative to each other when a drive system (not shown) pulls on a tendon 130 and pays out an opposing tendon 132 as shown in FIG. 1B. Tooth 114 is preferably shaped, positioned, and sized so that tooth 114 stays coupled to aperture 124 over the full range of rotation of members 110 and 120. Geared motion is desirable because the movement of members 110 and 120 can be modeled and predicted in a computer or other processing system that determines how to manipulate tendons 130 and 132 to achieve a desired movement of joint 100. Circular load bearing surfaces 112 and 122 preserve the separation between the centers of circles defining surfaces 112 and 122, which is desirable because the resulting movement is easily modeled and because symmetric attachments of tendons 130 and 132 result in the length of tendon 130 or 132 pulled in being equal to the length of the other tendon 132 or 130 paid out. The mechanics of the drive system that manipulates tendons 130 and 132 can therefore be simplified.

Figure 2:
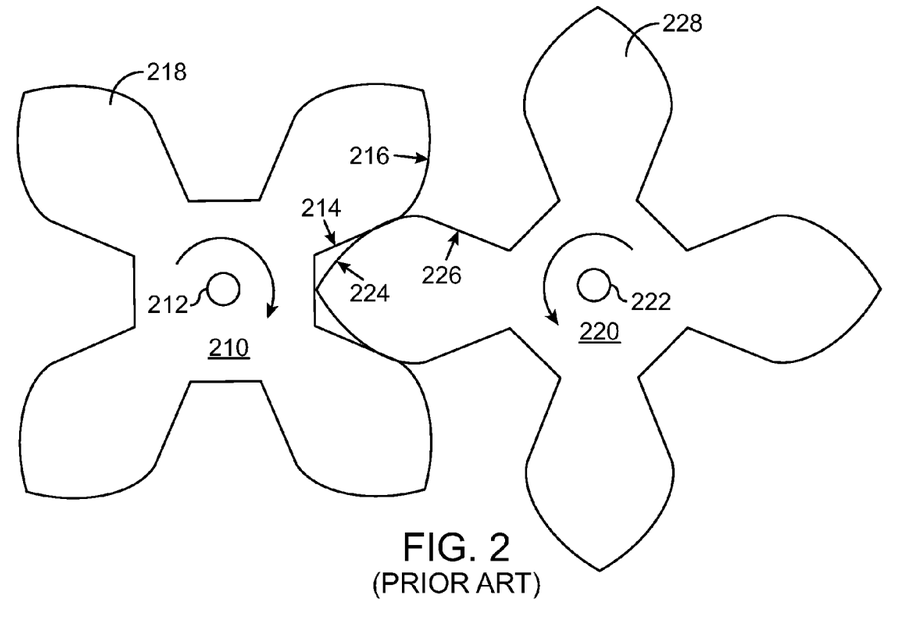
FIG. 2 shows a pair of cycloid gears.

Gears in general are known to use a variety of surface shapes that allow teeth of the gears to mesh without binding. For example, cycloid gears are gears having teeth with contacting surfaces following cycloidal curves. FIG. 2 shows a pair of cycloid gears 210 and 220 that are positioned on respective axles 212 and 222 that have the separation required for the teeth of gears 210 and 220 to correctly mesh. In particular, when gear 210 is driven to rotate clockwise, a surface 214 of gear 210 contacts a surface 224 of gear 220. Surfaces 214 and 224 are shaped to roll against each other as gears 221 and 220 rotate, e.g., surface 214 can be flat while surface 224 follows a cycloidal curve. Surfaces 216 and 226 then come into contact, and gears 210 and 220 rotate until the next tooth 218 of gear 210 comes into contact with the next tooth 228 of gear 220. Proper meshing of cycloid gears such as gears 210 and 220 is sensitive to the spacing of axles 212 and 222, which may be a leading reason why involute surfaces are much more commonly used in gears today.

Gears such as illustrated in FIG. 2 differ from a geared wrist joint such as illustrated in FIGS. 1A and 1B in that axles 212 and 222 fix the spacing of gears 210 and 220, so that contacting surfaces of the gears do not bear significant compression forces. In contrast, wrist joint 100 of FIGS. 1A and 1B when in a medical instrument would often need to bear compression forces (e.g., due to tensioning of both tendons 130 and 132) that tend to flatten the convex load bearing surfaces 112 and 122 of members 110 and 120. Since medical instruments containing wrist joints such as wrist joint 100 often have relatively small diameters, e.g., typically on the order of 3 to 10 mm for the entire diameter of member 110 or 120, and may encounter compression forces on the order of one hundred pounds, deformations of load bearing surfaces 112 and 122 are important concerns. Further, much of the cross-sectional area of a wrist joint may be needed for tendon guides or for one or more central lumens for devices such as camera cables or other systems that may extend through the instrument. The small available space for mechanical structures can make it challenging to manufacture wrist joint 100 with suitable strength and precision. In particular, the relatively small size of tooth 114 can result in tooth 114 disengaging from aperture 124 at the extremes of wrist motion, particularly when wrist 100 supports a load that deforms contacting surfaces 112 and 122.

SUMMARY

In accordance with an aspect of the invention, a wrist mechanism includes members with cycloidal surfaces that bear loads applied to the wrist mechanism. A pair of contacting cycloidal surfaces on respective members can be arranged to maintain a constant separation between reference points of members, and multiple pairs of contacting cycloidal surfaces can be arranged to ensure geared motion of the members. Alternatively, gear teeth can be included on the members to ensure geared motion and to improve a wrist's resistance to externally applied roll torques. Further, each load bearing contact area can include a hypocycloidal surface, which is concave, and the concave load-bearing surfaces can increase the capacity of the wrist joint to bear compression forces without unacceptable deformation or alternatively permit use of materials that otherwise would not be suitable for a wrist of a given size and load-bearing capacity.

In accordance with a specific embodiment of the invention, an instrument wrist includes a first member having a first cycloidal surface and a second member having a second cycloidal surface that contacts the first cycloidal surface. Compressing forces on the members are born by contact of the cycloidal surfaces on the first and second members. The members can be arranged for geared motion in response to the force applied by a tendon to one of the members.

BRIEF DESCRIPTION OF THE DRAWINGS

Use of the same reference symbols in different figures indicates similar or identical items.

DETAILED DESCRIPTION

In accordance with an aspect of the current invention, mechanical members in a wrist mechanism use cycloidal surfaces to bear compression during geared motion of the mechanical members. In particular, a wrist joint can use an epicycloidal surface on a first member contacting a hypocycloidal surface on a second member. With proper selection of the parameters of the defining cycloids and gearing of the members, the cycloidal surfaces constrain motion of the members to preserve a separation between reference points corresponding to centers of the cycloidal curves followed by the cycloidal surfaces. The cycloidal surfaces also provide a concave contact area, which leads to less deformation when drive systems or external loads push the members together. Geared motion of the first and second members can be achieved using additional load-bearing cycloidal surfaces. In particular, a hypocycloidal surface on the first member and an epicycloidal surface on the second member can create a contact area that operates to balance the forces at the other contact area, so that the net forces at the contact areas cause geared motion. Alternatively, gear structures such as teeth can be used on the members to ensure geared motion and improve resistance to roll torques.

Figure 3:
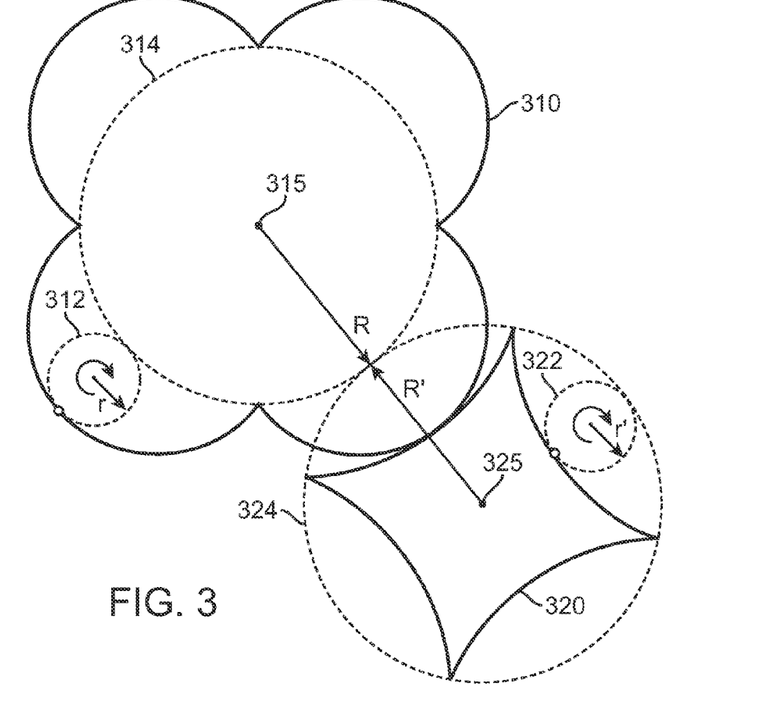
FIG. 3 illustrates an epicycloid and a hypocycloid that maintain a fixed separation between their respective centers during geared motion.

A "cycloidal surface" as used herein refers to a surface having a portion of a cycloid as an intersection of the surface with a plane. Cycloids are well known and in general can be defined using parametric equations. More visually, a cycloid corresponds to the path of a point on a circle rolling on a line or another circle. FIG. 3, for example, illustrates an epicycloid 310 that corresponds to the path of a point on a circle 312 of radius r rolling around the outside of a circle 314 of radius R, where R>r. A hypocycloid 320 corresponds to the path of a point on a circle 322 of radius r' rolling around the inside of a larger circle 324 of radius R', R'>r'. Under the conditions that the radii of the describing circles are the same, i.e., R'=R and r'=r, the distance between centers 315 and 325 of epicycloid 310 and hypocycloid 320 remains constant when cycloids 310 and 320 rotate with the same angular velocity, i.e., are in geared motion with 1:1 gear ratio. (Epicycloids and hypocycloids can also be matched to provide a constant center-to-center separation for other gear ratios.) During geared motion, if the contact points on cycloids 310 and 320 are on the describing circles 314 and 324, then there is no relative velocity between the contact points. In general, however, the contacting surfaces are moving at different speeds, and the surfaces rub (slide) against one another. Even though the surfaces rub, 1:1 gear motion (for R=R') ensures that the two describing circles 314 and 324 do not slip relative to each other.

Figure 4:
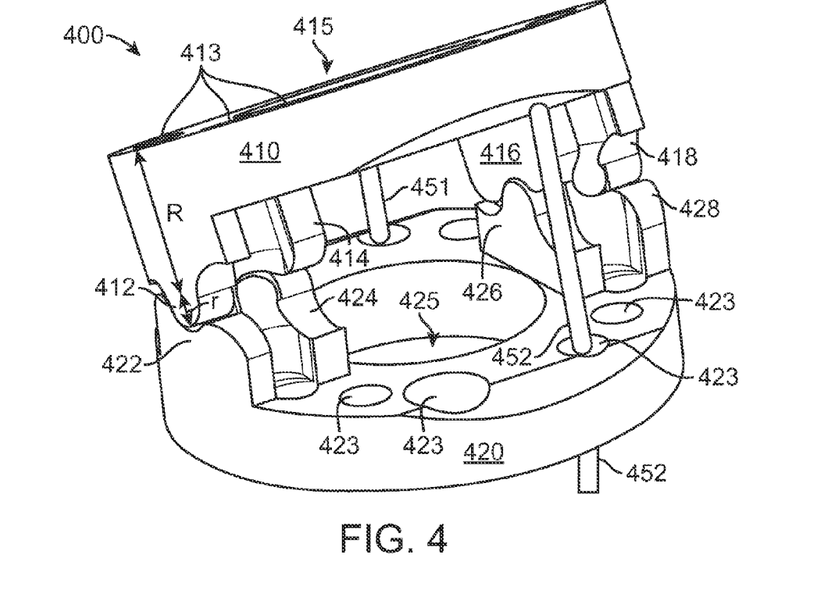
FIG. 4 shows a wrist joint in accordance with an embodiment of the invention using stepped cycloidal surfaces for bearing loads and constraining motion of the wrist joint.

Cycloidal surfaces and curves have an advantage in wrist joints over common toothed gears in that contacting surfaces of members in wrist joints automatically maintain the proper positioning for operation when applied forces keep the members in contact, as is the case in tendon-stayed robotic wrists. FIG. 4 shows a wrist joint 400 including rolling members 410 and 420 that employ load-bearing cycloidal surfaces. Wrist joint 400 may be used in a mechanical wrist that includes several similar joints and in an exemplary embodiment is incorporated in a medical instrument that can be used for minimally invasive medical procedures. In wrist joint 400, each member 410 or 420 has a substantially disk-shaped body with a center hole 415 or 425 that defines a portion of a central lumen that may extend along the length of an instrument. Each disk 410 and 420 can be made of any material that provides sufficient strength and durability for the particular use of wrist joint 400 and particularly for the size of the wrist mechanism and the expected loads. Wrist members 410 and 420 may need to be a metal such as stainless steel for higher load applications, particularly when wrist diameter is smaller than about 5 mm. Materials such as plastic or ceramics may be employed in larger diameter wrist mechanism or lower load conditions. As described further below, an advantage of wrist joint 400 is resistance to compressional strain, and this resistance may permit use of materials such as plastic or ceramic in an electrically insulating wrist having a smaller diameter and/or a central lumen than could be achieved using circular load bearing surfaces. Insulating wrist mechanisms are particularly desirable in medical instruments that include electrically charged or activated tools or end effectors. In general, the wrist can be scaled to the forces, or the task.

Disk 410 has projection 412, 414, 416, and 418 with cycloidal surfaces that are in contact with the respective cycloidal surfaces of projections 422, 424, 426, and 428 on disk 420. Projections 412, 414, 416, and 418 are positioned along a diameter of disk 410 with projections 412 and 418 being near or extending to opposite edges of the circumference of disk 410 and projections 414 and 426 being near or extending to opposite edges of center hole 415. Similarly, projections 422, 424, 426, and 428 are positioned along a diameter of member 420 with projections 422 and 428 being near or extending to opposite edges of the circumference of disk 420 and projections 424 and 426 being near or extending to opposite edges of the center hole 425 through disk 420. In the illustrated embodiment, projections 412, 414, 416, and 418 include central portions that are epicycloid or hypocycloidal surfaces that are complementary to respective hypocycloidal or epicycloidal surfaces on contacting projections 422, 424, 426, and 428. The central cycloidal portions on projections 412, 414, 416, and 418 follow portions of respective cycloids, and the centers of these cycloids all lie along a line defining a direction of a tilt axis. Similarly, the central cycloid portions on projections 422, 424, 426, and 428 follow portions of respective cycloids, and the centers of these cycloids lie along a line that is parallel to the tilt axis. When disk 410 tilts relative to disk 420 under geared motion with the proper gearing ratio, the cycloidal surfaces of projections 412, 414, 416, and 418 remain in contact with the cycloidal surfaces of projections 422, 424, 426, and 428 and maintain a fixed separation between reference points or lines corresponding to the centers of the surface-defining cycloids. The heights of the projections provide clearance for tilting before body portions of members 410 and 420 contact each other and prevent further motion.

Disks 410 and 420 in addition to having center holes 415 and 425 for a central lumen of a medical instrument include guide holes 413 and 423 for tendons 451 and 452 that articulate joint 400 and tendons (not shown) that may extend through joint 400 to other portions of the medical instrument. Tendons 451 and 452 can be cables, filaments, tubes, or similar structures that are sufficiently flexible to bend as needed within the instrument and are strong enough to apply forces that articulate joint 400 to tilt member 410 relative to member 420. Tendons 451 and 452 as shown attach to member 410 at opposite moment arms relative to the diameter along which projections 412, 414, 416, and 418 are positioned. A drive system (not shown) can then pull on (or increase the tension in) one tendon 451 or 452 to tilt member 410 in one direction relative to member 420, or pull on (or increase tension in) the other tendon 452 or 451 to tilt member 410 in the opposite direction. In general, the tendons 451 and 452 have preload tensions that force members 410 and 420 together so that projections 412, 414, 416, and 418 remain in contact with respective projections 422, 424, 426, and 428.

Geared motion is maintained in wrist mechanism 400 by the arrangement of epicycloid and hypocycloidal surfaces in multiple contacting areas. In particular, projection 412 has a central epicycloid portion that contacts a matching hypocycloid portion of projection 422. When tendon 451 or 452 is pulled to tilt member 410, the epicycloidal surface of projection 412 rolls on the hypocycloidal surface of projection 422. If projections 412 and 422 were an isolated system, i.e., if projections 414, 416, 418, 424, 426, and 428 were not present, the projections 412 and 422 would slip relative to geared motion. However, at the contact of projections 414 and 424, the epicycloidal surface is on member 420 and contacts a hypocycloidal surface on member 410. As a result, the tendency of the contact of projections 412 and 422 to slip relative to geared motion is countered by the opposing tendency of the contact of projections 414 and 424 to slip in the opposite sense. In wrist joint 400, the contacting cycloidal surfaces of the projections have balancing tendencies to slip that collectively keep members 410 and 420 in geared motion when tendons 451 and 452 articulate wrist joint 400.

The range of angular movement of disk 410 relative to disk 420 while the central cycloidal surfaces contact each other depends on the parameters defining the cycloidal surfaces. In particular, in FIG. 3, epicycloid 310 has parameters R and r such that R=4r, which creates four epicycloid lobes joined to four hypocycloid lobes, and geared rotation of epicycloid 310 that maintains contact of hypocycloid 320 to one lobe of epicycloid 310 can provide an angular range of at most 90°, i.e., up to +/−45°. In wrist joint 400, cycloidal surfaces based on cycloids having more lobes are desired because of size goals or limitations on projections 412, 414, 416, and 418 and the reduction in rubbing at the contacting surfaces during geared motion when each lobe has a smaller angular range. The range of motion is typically a design input for a wrist mechanism, and picking the number of lobes in the defining cycloids and the angular range of each lobe may be a question of optimizing a wrist for a particular use. In one embodiment, the size of each lobe, e.g., the central cycloidal surface, is about one half of the required range of motion, which provides a practical and producible structure, and a 22.5 degree cycloid (i.e., 16 lobes in a full epicycloid or hypocycloid) is well suited for a ±45° ROM when each projection smoothly transitions from an epicycloidal or hypocycloid central surface to two hypocycloidal or epicycloidal surfaces on either side of the central surface. The epicycloidal and hypocycloidal surfaces on a projection follow portions of cycloidals having the same center point and radii parameters R and r. To provide complementary surfaces, projection 422 includes a central hypocycloidal surface that smoothly transitions to two outer epicycloidal surfaces where all of the cycloids defining these surfaces have the same center point and radii parameters R and r.

Each of the cycloidal surfaces on projections 412, 414, 416, 418, 422, 424, 426, and 428 is such that a plane parallel to a tilt axis of wrist joint 400 intersects the cycloidal surface along a straight line, and a plane perpendicular to the tilt axis intersects the cycloidal surface along a cycloidal curve or a concatenation of cycloidal curves as described above. With this configuration, wrist joint 400 provides a single degree of freedom of motion, e.g., a tilt angle of disk 410 relative to disk 420. For a multi-jointed wrist mechanism, additional projections (not shown) that are similar to projections 412, 414, 416, and 418 can be added to the back side of disk 410 and engaged with projections on a disk that is similar or identical to disk 420. If the projections added to the back of disk 410 are along the same diameter of disk 410 as projections 412, 414, 416, and 418, the additional wrist joint can provide a greater range of tilt than can the single wrist joint 400. Alternatively, if added projections on the back of disk 410 are along a diameter that is perpendicular to the diameter on which projections 412, 414, 416, and 418 are arranged, the pair of joints can provide two degrees of freedom of motion, e.g., pitch and yaw.

Wrist joint 400 operates with epicycloidal surfaces contacting hypocycloidal surfaces, so that at least one of the load-bearing surfaces (i.e., the hypocycloidal surface) is a concave. This is desirable because the surfaces also support compression forces, e.g., react to the tension in articulating tendons 451 and 452 and external forces applied to an instrument containing wrist joint 400. The concave surfaces can generally withstand greater force than can convex surfaces before being unacceptably deformed. For example, if circular surfaces were used to roll against each other and maintain a separation between center points, both contacting surfaces would be convex and could more easily be flattened when a load is applied. The deformation can damage or crush the load bearing structures particularly if a less resilient material such as a ceramic is used in the wrist joint.

Another desirable feature of wrist joint 400 is that projections 412, 414, 416, and 418 and 422, 424, 426, and 428 alternate between having central epicycloidal surfaces and central hypocycloidal surfaces. The taller portions of projection 412 and 424 and 426 and 428 can interlock and prevent disk 410 from slipping sideways relative to disk 420 along the direction of the tilt axis.

Figure 5A:
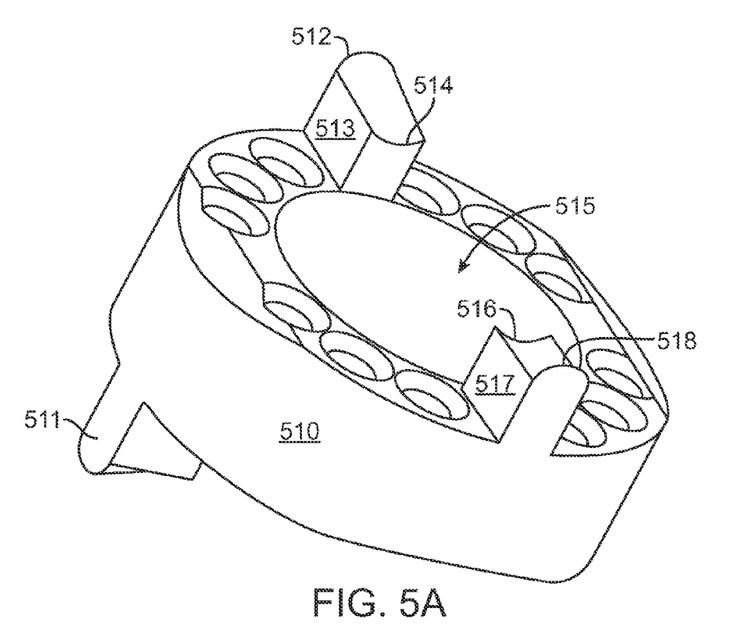
FIGS. 5A and 5B show respective mechanical members used in a wrist joint in accordance with an embodiment of the invention using blended cycloidal surfaces for bearing loads and constraining movement.

FIG. 5A illustrates a member or disk 510 employing projections 513 and 517 having blended cycloidal surfaces. In particular, projection 513 has an outer edge 512 (near the circumference of disk 510) that is an epicycloidal curve and an inner edge 514 (near a center hole 515) that is a hypocycloid. A blended surface between edges 512 and 514 contain lines that connect points on epicycloid edge 512 to points on hypocycloid edge 514 that have the matching values of an angle parameter θ, where angle parameter θ indicates the relative of rotation of the smaller circle used to define the cycloidal curve 512 or 514. Projection 517 similarly has a blended surface that transitions from an epicycloidal curve

518 at the circumference of disk 510 to a hypocycloidal curve 516 at the edge of center hole 515.

Figure 5B:
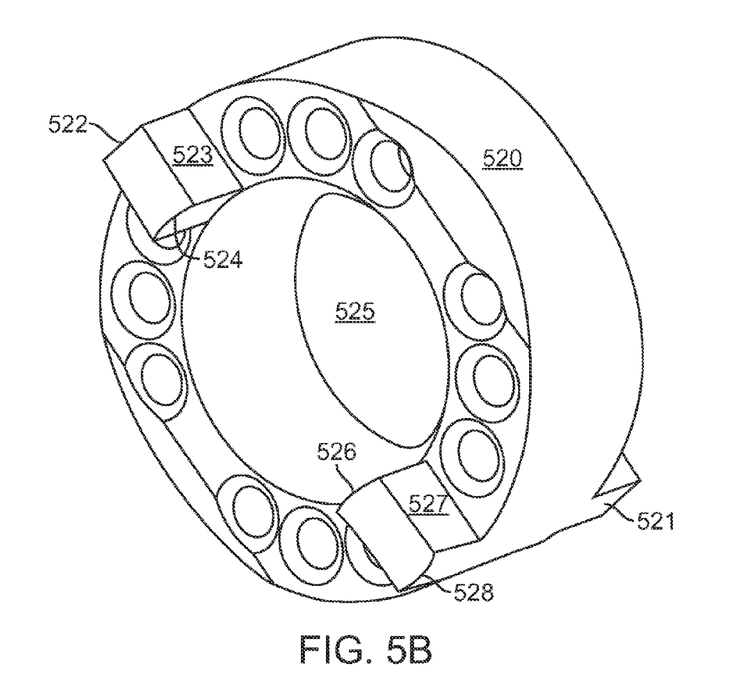

FIG. 5B shows a disk 520 having projections 523 and 527 with blended surfaces aligned along a diameter of disk 520 and designed for geared motion on the blended surfaces of disk 510 of FIG. 5A. The blended surface on projection 523 smoothly transitions from a hypocycloidal curve 522 at the circumference of disk 522 to an epicycloidal curve 524 at a circumference of a center hole 525 through disk 520. Similarly, the blended surface on projection 527 smoothly transitions from a hypocycloidal curve 522 at the circumference of disk 522 to an epicycloidal curve 524 at a circumference of a center hole 525 through disk 520. Outer hypocycloidal curves 522 and 528 on disk 520 are complementary to outer epicycloidal curves 512 and 518 on disk 510, and inner epicycloidal curves 524 and 526 on disk 520 are complementary to inner hypocycloidal curves 514 and 516 on disk 510.

Disk 510 when held with the blended surfaces of projections 513 and 517 in contact with projections 523 and 527 on disk 520 can roll on disk 520, and the complementary cycloidal curves constrain the movement of disks 510 and 520 in the same manner as circular objects rolling on each other to tilt disk 510 relative to disk 520. Further, the tendencies of the contact points at opposite edges of the blended surfaces to slip relative to geared motion cancel each other and together maintain geared motion. At the same time, the alternating high portions of projections 513 and 517 and 523 and 527 resist slipping disks 510 and 520 along the direction of the tilt axis. The blended surfaces can also provide better ability to support compression than would the conventional contact of circular surfaces. In particular, the blended surfaces have concave and convex portions separated by inflections, and the contact of two complementary blended surfaces includes a first area where a convex surface of a first blended surface contacts a concave or flat portion of the second blended surface, a second area where convex portions of the first and second surfaces contact each other, and a third area where a concave or flat surface of a first blended surface contacts a convex portion of the second blended surface. The contacts with concave surfaces can improve the ability of a wrist joint to support compression forces.

Disk 520 has two projections 521 (one of which is visible in FIG. 5B) on a back side and positioned along the same diameter as projections 523 and 527. In the illustrated embodiment, projections 521 have blended surfaces identical to the blended surfaces of projections 523 and 527 and thus are complementary to the blended surfaces of projections 513 and 517 on disk 510 in FIG. 5A. A three-member wrist joint can be formed using disk 510 with projections 513 and 517 in contact with respective projections 523 and 527 on disk 520 and an identical copy of disk 510 with projections 513 and 517 in contact with projections 521 of disk 520. This three-member structure would provide two joints both of which tilt about the same direction axis, and the three-member wrist mechanism can provide a greater range of tilt than would a single wrist joint.

Disk 510 also has two projections 511 (one of which is visible in FIG. 5A) on a back side, but projections 511 are positioned along a diameter that is perpendicular to the diameter along which projections 513 and 517 are positioned. In the illustrated embodiment, projections 511 have blended surfaces identical to the blended surfaces of projections 513 and 517 and complementary to the blended surfaces of projections 523 and 527 on disk 520. A three-member wrist joint can thus be formed using member 520 with projections 523 and 527 in contact with respective projections 513 and 517 on disk 510 and an identical copy of member 520 with projections 523 and 527 in contact with projections 511 of disk 510. This three-member wrist mechanism acts as a U-joint and provides two degrees of freedom of motion, one corresponding to tilt about an axis defined by the arrangement of projections 513 and 517 and another corresponding to tilt about an axis defined by the arrangement of projections 511.

Figure 6A:
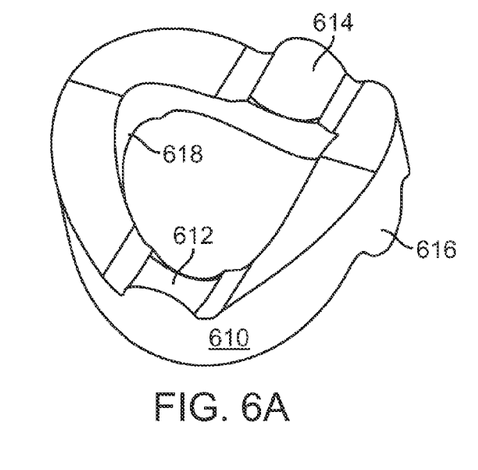
FIG. 6A shows a wrist member having a saddle shape that allows positioning of cycloidal surfaces to provide crossing tilt axes and a compact wrist structure.

FIG. 6A shows a member 610 that like disk 510 has a first pair of cycloidal surfaces 612 and 614 arranged for a first tilt axis and a second pair of cycloidal surfaces 616 and 618 arranged for a second tilt axis that is perpendicular to the first tilt axis. In the illustrated embodiment, each of the surfaces 612, 614, 616, and 618 is a blended surface that smoothly transitions from an outer epicycloidal curve to an inner hypocycloidal curve. In alternative embodiments, any of surfaces 612, 614, 616, and 618 could be a blended surface that transitions from an outer hypocycloidal curve to an inner epicycloidal curve, a stepped surface having an epicycloid portion and a hypocycloid portion, an epicycloidal surface, or a hypocycloidal surface. Member 610 differs from disk 510 in that the cycloidal surfaces are not on projections but are integrated into a general saddle shape so that the two perpendicular tilt axes defined by cycloidal surfaces 612, 614, 616, and 618 can be provided in a more compact structure or compact universal joint (U-joint). Ideally, the perpendicular tilt axes cross in the same plane. Crossing tilt axes can be advantageous for computer control systems because a computer model can provide an exact solution for describing the control and movement of a compound joint having crossed axes.

Figure 6B:
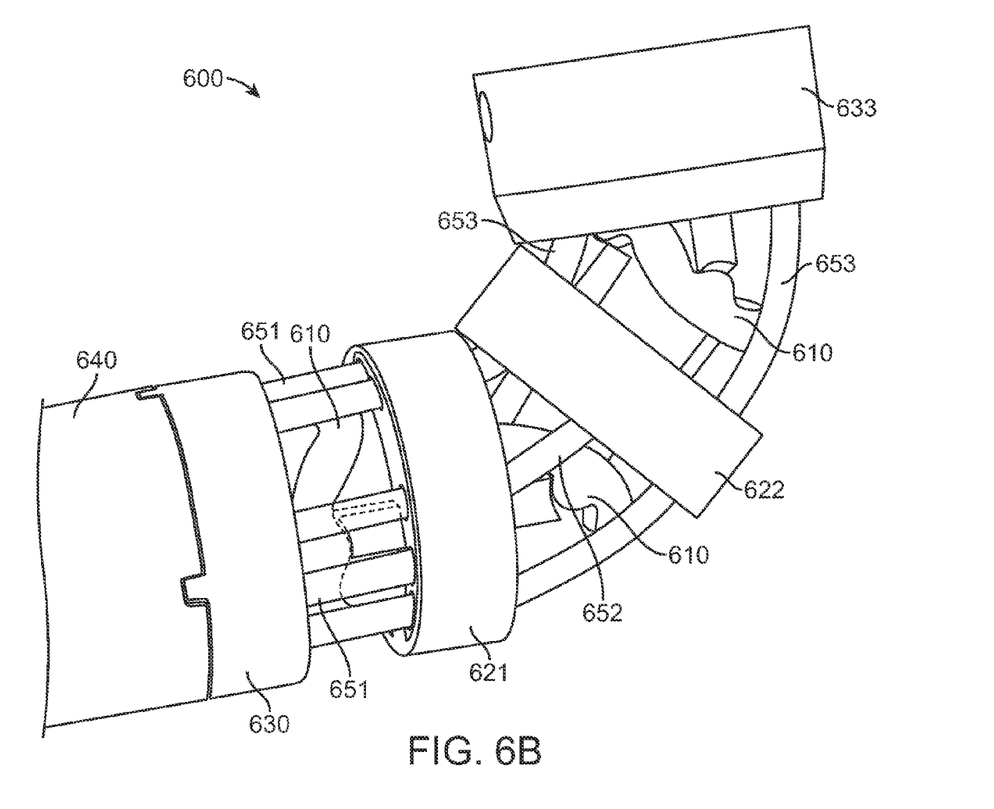
FIG. 6B shows a multi-jointed wrist mechanism using the saddle-shaped wrist members such as illustrated in FIG. 6A.

FIG. 6B shows a wrist mechanism 600 that includes three members 610 of the type illustrated in FIG. 6A. Members 610 have their cycloidal surfaces engaged with complementary cycloidal surfaces of intervening members 621 and 622 or end members 630 and 633. Members 621 and 622 are generally similar to members 520 of FIG. 5B, but projections having cycloidal surfaces on each member 621 or 622 are offset inwardly from the circumference of the member, allowing members 621 and 622 have guide holes for tendons in a ring area outside of the projections. Each end members 630 or 633 has one side with projections that are the same as the projections of members 621 and 622 and an opposite side adapted to connect to a main tube or an extended member 640 of an instrument (not shown.) Members 610 are sized to fit with in the ring of tendons and engage the projections on members 621, 622, 630, or 633 without obstructing the tendons. Main tube or extended member 640 may attach directly or indirectly to a drive mechanism (not shown) that controls tendons 651, 652, and 653.

Tendons 651, which extend through main tube 640 and end member 640 to attach to member 621, control a three-member wrist joint including end member 640, a saddle shaped member 610, and intervening member 621. This three-member wrist joint provides two degrees of freedom for tilting member 621, which can be actuated using at least three tendons 651. Three tendons 652, which extend through main tube 640, end member 630, and member 621 to attach to member 622, can be used control a three-member U-joint including members 621, 610, and 622. Three tendons 653, which extend through main tube 640, end member 630, member 621, and member 622 to attach to end member 633, can similarly control a three-member U-joint including members 622, 610, and 633. Wrist mechanism 600 thus employs nine tendons to control three U-joints that allow complex manipulation of the shape of wrist mechanism 600 and the orientation of end member 633. FIG. 6B shows a configuration in which wrist mechanism 600 provides a simple 90° bend. In one embodiment, a portion of mechanism 600 including the top two saddles 610 forms a 2 degree of freedom, +/−90 degree wrist.

The remaining saddle 610 is part of the top elbow joint in a pair of elbow joints that are on either side of extended member 640. Each elbow has a +/−45 degrees range of motion, and the two elbows are built to remain parallel to a main tube of when extended member 640 is part of a "joggle joint" such as described in U.S. Pat. App. Pub. No. US 2008/0065102 A1, entitled "Surgical Instrument with Parallel Motion Mechanism," filed Jun. 13, 2007. The members with cycloids are used in mechanism 600 to create a full six degrees of freedom to position a tool attached to end 633 in x, y, z, and roll, pitch, yaw.

Figure 7:
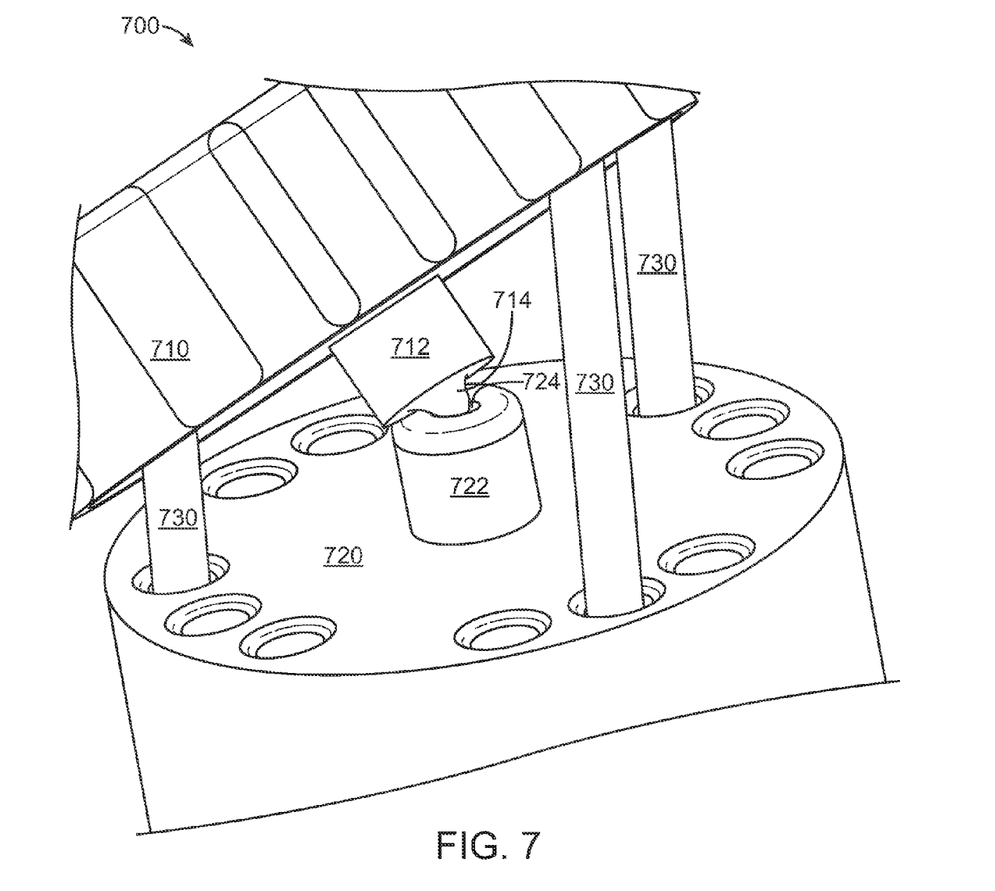
FIG. 7 shows a two-piece wrist joint using cycloidal surfaces to provide both pitch and yaw motion in a compact structure.

Two degrees of freedom for tilting a member in a wrist joint can be achieved using a two-member structure having load-bearing cycloidal surfaces. FIG. 7, for example, shows a wrist joint 700 including two members or disks 710 and 720. Disk 710 has a projection 712 with a cycloidal surface 714. Cycloidal surface 714 has a central portion that corresponds to the surface swept out by rotation of an epicycloidal curve about a center line. Disk 720 has a projection 722 with a cycloidal surface 724 that is complementary to cycloidal surface 714. In particular, at least a central portion of cycloidal surface 724 corresponds to the surface that a hypocycloidal curve sweeps out when rotated about a center line, and the hypocycloidal curve used to define at least the central portion of surface 724 is complementary to the epicycloidal curve used to define the central portion of surface 714. More generally, to accommodate a greater range of motion, the curves used to define surfaces of revolution 714 and 724 can include a portion of epicycloid or hypocycloid between two portions of hypocycloids or epicycloids, where all the cycloids have the same center and the radii parameters R and r. Complementary cycloidal surfaces 714 and 724 are not confined to roll along in one dimension but instead provide two degrees of freedom for tilting of member 710 relative to member 720. Three tendons 730 can thus be used to control the pitch and yaw of member 710 relative to member 720.

Figure 8:
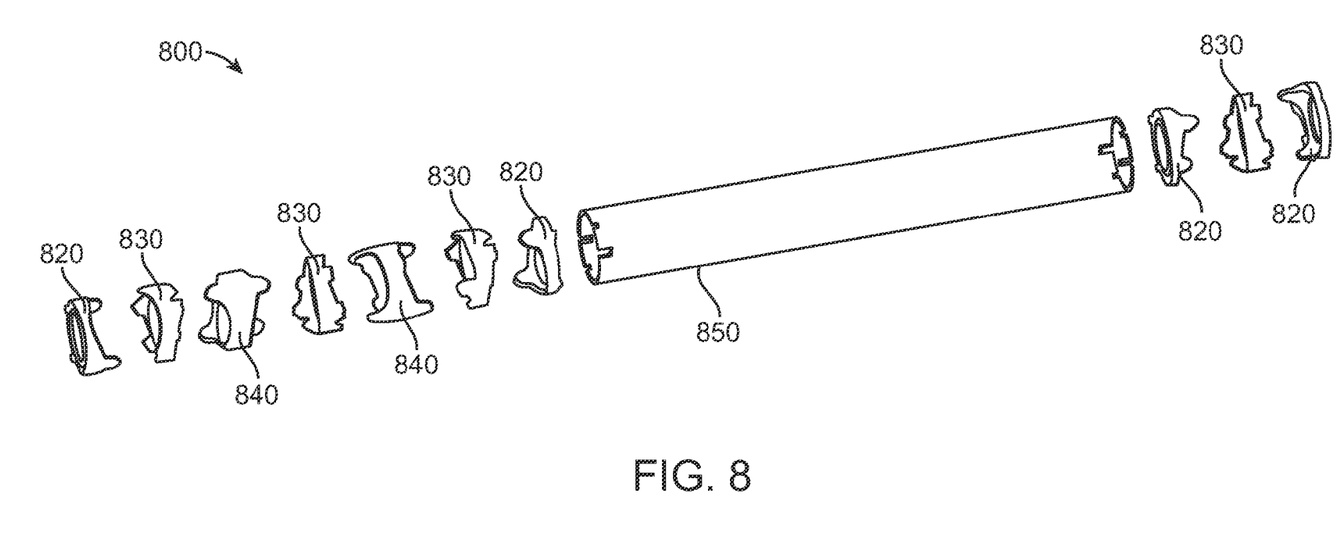
FIG. 8 is an expanded view of a wrist mechanism in accordance with an embodiment of the invention containing multiple joints and members with cycloid load-bearing surfaces and gear structures to ensure geared motion.

Wrist joints described above can use cycloidal surfaces to bear loads, preserve the distance between reference points, and ensure geared motion. However, in accordance with a further aspect of the invention, wrist joints having load-bearing cycloidal surfaces can also employ gearing to ensure geared motion and improve resistance of a wrist joint to torques around the wrist's roll axis (roll torques). FIG. 8 shows a multi-joint wrist mechanism 800 employing gearing to ensure 1:1 geared motion in each joint using load-bearing cycloidal surfaces. Wrist mechanism 800 includes toothed end members 820, slotted members 830, toothed intermediate members 840, and an extension 850.

Figure 9A:
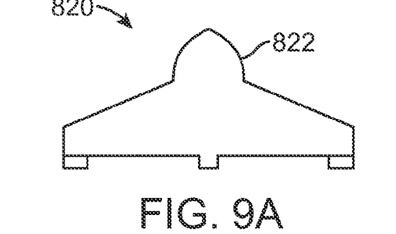
FIGS. 9A, 9B, 9C, and 9D show side, top, and two cross-sectional views of toothed end members used in the wrist mechanism of FIG. 8.
Figure 9B:
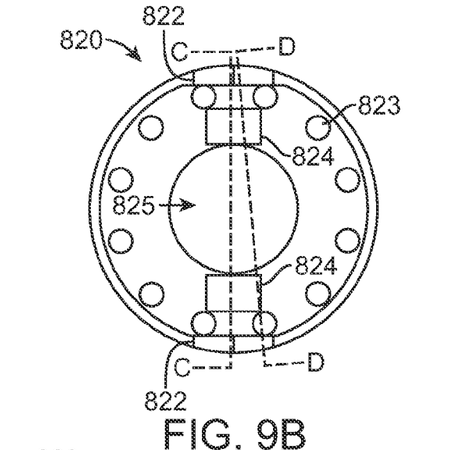
Figure 9C:
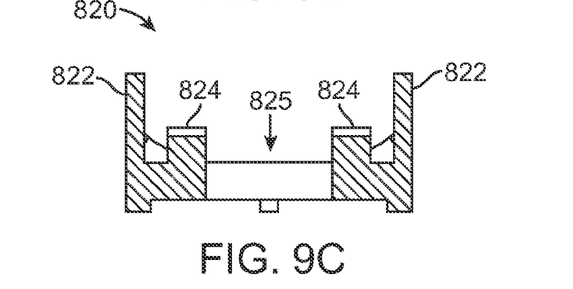
Figure 9D:
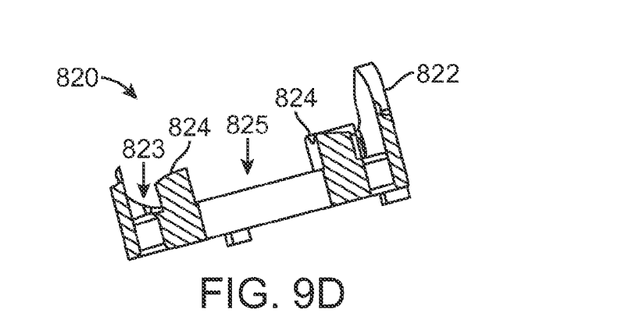

End members 820 have one side that is shaped for a fixed connection to another structure such as extension 850, a main tube (not shown), or a tool (not shown; e.g., a surgical end effector). FIGS. 9A, 9B, 9C, and 9D illustrate an embodiment of toothed end member 820 in more detail. In particular, FIG. 9A is a side view of toothed end member 820 showing the profile of a gear tooth 822. As shown in the top view of FIG. 9B, end member 820 has two teeth 822 located at opposite points on the circumference of member 820. FIG. 9B also shows projections 824 that have load-bearing cycloidal surfaces positioned inward from teeth 822 and adjacent to a center hole 825 through member 820. Holes 823 through member 820 provide guides for tendons. Section lines C-C and D-D show the relative orientation of cross-sectional views of member 820 illustrated in FIGS. 9C and 9D. FIG. 9C shows a cross-section of member 820 illustrating how teeth 822 and projections 824 are aligned along a diameter or member 820. The cycloidal surfaces follow portions of cycloids having center points that are aligned and define a direction of a tilt axis for a wrist joint including member 820. FIG. 9D shows a cross-section providing a view of the cycloidal surface of a projection 824. In the illustrated embodiment, the cycloidal surfaces on projections 824 include a central hypocycloidal surface, but other types of cycloid, stepped, or blended surfaces could alternatively be used. Tooth 822 does not bear a significant portion of the compression load on a joint and is used to ensure geared motion of adjacent disk and resist roll torques. Tooth 822 can be part of a cyloid pin gear and have the shape of a cycloidal gear tooth similar to those depicted in FIG. 2. Alternatively, tooth 822 can be shaped the same as a tooth of an involute gear provided that the notches engaging tooth 822 are correspondingly shaped. Only one tooth is necessary in the illustrated embodiment since the joint range of motion is a +/−45 degrees, but a larger portion of a gear could alternatively be used ensure geared motion of the members.

Figure 10A:
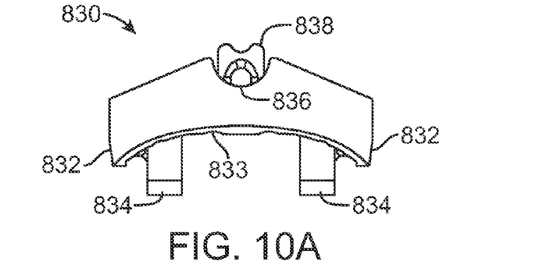
FIGS. 10A, 10B, 10C, and 10D show side, top, and two cross-sectional views of a slotted members in the wrist mechanism of FIG. 8.
Figure 10B:
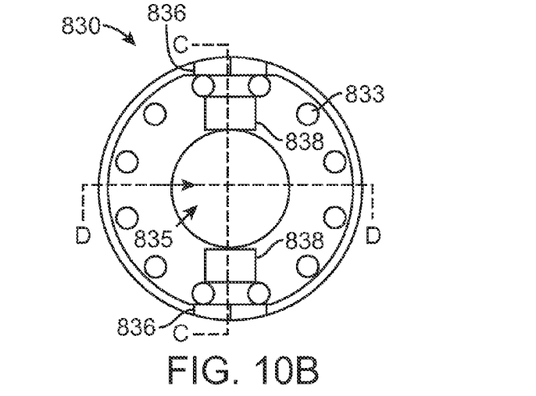
Figure 10C:
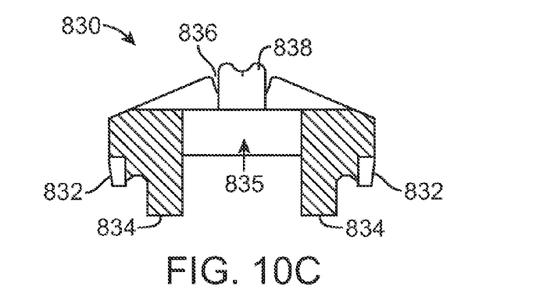
Figure 10D:
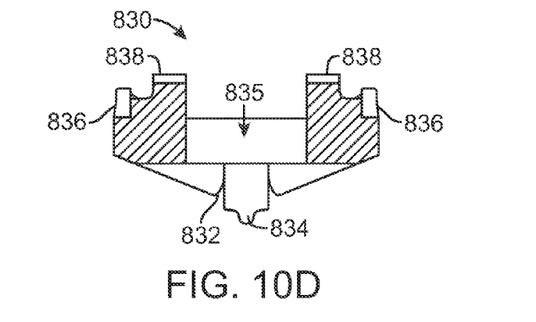

FIGS. 10A, 10B, 10C, and 10D show details of an embodiment of slotted member 830, which is designed to engage an end member 820 to form a wrist joint. FIG. 10A is a side view of slotted member 830. A bottom surface of member 830 has projections 832 having cycloidal surfaces that are complementary to the cycloidal surfaces of projections 824 on end member 820. FIG. 10D shows that bottom projections 835 have a central epicycloid portion in the illustrated embodiment. The cycloidal surfaces of projections 834 follow portions of cycloids having centers that are aligned and define a first tilt axis for a wrist joint created with a member contacting bottom projections 834. Member 830 also has notches or slots 842 that are open toward the bottom of member 830 and positioned and shaped to engage teeth 822 on member 820. (Alternatively, member 830 could include teeth that engage notches in member 820.) The top side of each member 830 as shown in FIG. 10B also includes slots 836 and projections 838. Projections 838 as shown in FIGS. 10A and 10C has a cycloidal surface with a central hypocycloid portion, the same as projections 824 of member 820 in the illustrated embodiment. However, the cycloidal surfaces of projections 838 are portions of cycloids having centers that are aligned to define a second tilt axis that is perpendicular to the first tilt axis defined by bottom projections 834. Accordingly, member 830 can be used as the center member in a U-joint. FIG. 10B also shows that member 830 includes a center hole 835 for a central lumen in an instrument and guide holes 833 for tendons.

Figure 11A:
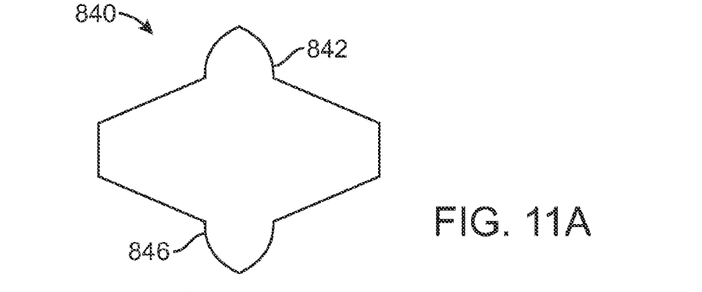
FIGS. 11A, 11B, 11C, and 11D show side, top, and two cross-sectional views of a toothed intervening member in the wrist mechanism of FIG. 8.
Figure 11B:
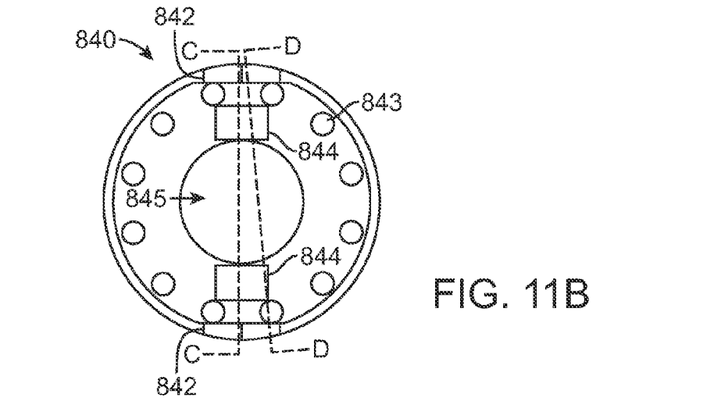
Figure 11C:
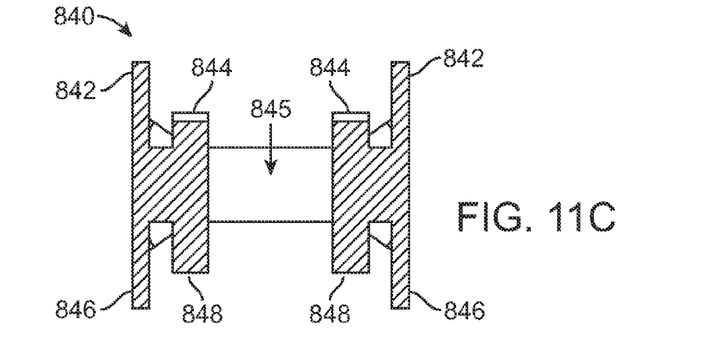
Figure 11D:
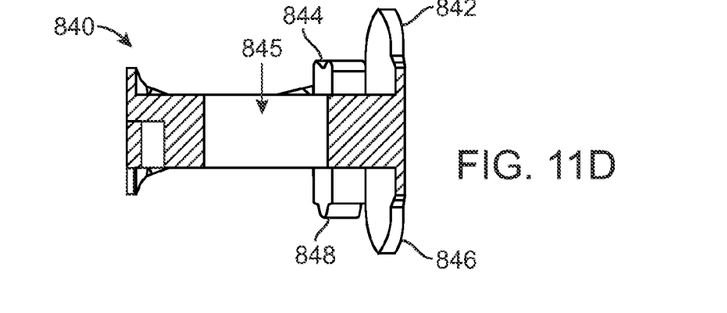

FIGS. 11A, 11B, 11C, and 11D show details of an embodiment of toothed intermediate member 840. Each toothed intermediate member 840 has a top side and a bottom side, both of which are substantially identical to the top side of end member 820. FIG. 11A shows a side view of member and illustrates the profile of a top tooth 842 and a bottom tooth 846, which like tooth 822 are shaped and positioned to engage slots 832 or 834 in slotted member 830. (Alternatively, member 830 could include teeth that engage notches in member 840.) FIG. 11B is a top view of member 840 showing the relative positions of teeth 842, guide holes 843, projections 844, and a center hole 845. The bottom side of member 840 has a similar arrangement of teeth 846 and projections 848 relative to guide holes 843 and center hole 845. As shown in FIG. 11C, projections 844 and teeth 842 are aligned on the same diameter of member 840 as are projections teeth 846 and projections 848. Projections 844 and 848 have cycloidal surfaces that are aligned to define the same direction for a tilt axis. However, as can be seen in FIG. 11D, the cycloidal surfaces of projections 844 have a hypocycloid center portion, while projections 848 have a complementary epicycloid center portion in the illustrated embodiment.

Multi-joint wrist mechanism 800 of FIG. 8 illustrates one configuration for use of members 820, 830, and 840 in a tendon stayed wrist mechanism. Beginning at the left in wrist mechanism 800, end member 820 can be used as a base for attachment of a tool in a medical instrument. End member 820 has teeth 822 and projections 824 that engage bottom slots 832 and bottom projections 834 of a slotted member 830. That slotted member 830 has top slots 836 and projections 838 that engage bottom teeth 846 and bottom projections of intermediate toothed member 840. Because of the 90° rotation in member 830 of top slots 836 and projections 838 relative to bottom slots 832 and projections 834, the first three members 820, 830, and 840 form a U-joint. Teeth 822 and 846 engaged in slots 832 and 836 resist torques tending to twist the U-joint. Three tendons (not shown) that pass through members 820 and 830 can attach to member 840 and control both degrees of freedom in the tilt of member 840 relative to member 820. In particular, when the tendons pull member 840 with a net torque about the tilt axis defined by the top projections 838 of slotted member 830, bottom teeth 846 of member 840 engage top slots 836 of member 838 causing geared motion of members 840 and 830 with a 1:1 gear ratio for rotation about that tilt axis. When the tendons pull member 840 with a net torque about the tilt axis defined by the bottom projections 834 of slotted member 830, the interlocking of teeth 846 and projections 848 with slots 836 and projections 838 prevent relative movement in response to the net torque, so that members 840 and 830 move as a unit in response to the applied torque. Slots 832 of member 830 engage teeth 822 of member 820 causing geared motion of members 840 and 830 relative to member 820 with a 1:1 gear ratio for rotation about the tilt axis defined by projections 834.

Three U-joints are similarly provided in wrist mechanism 800 to the left of extension 850. Each of these U-joints corresponds to a member 830 sandwiched between members 820 or 840. Extension 850 couples to an end member 820 to provide a relatively large spatial range of motion in response to the range of angular movement of end member 820. A final U-joint made of a slotted member 830 between two end members 820 can provide additional angle and position control at the end of the large range of motion achieved using extension 850. FIG. 8 also shows guides 855, which guides tendons through extension 850 for control of the final U-joint or a tool attached to the final end member 820.

An advantage of structures such as mechanism 800, which includes relatively large teeth 822, is the ability to support a relatively large roll torque. Blended cycloidal surfaces such as used in mechanism 600 in FIG. 6 may withstand the torques encountered during light surgical tasks (such as laser dissection or suction irrigation) using an instrument having a diameter of about 5 mm. However, surgical tasks with tools applying larger grip forces tend to produce higher torques that may be better supported by teeth 822 in mechanism 800, particularly at small instrument diameters of about 5 mm or less. A comparative advantage of using load-bearing cycloidal surface as in FIG. 6 without gearing structures such as in FIG. 8 is that eliminating the teeth allows a larger area for load bearing surfaces, permitting a compact joint to support greater loads.

Embodiments of the invention as described above provide a number of advantages over many prior wrist mechanisms. For example, the concave surfaces can provide low contact stress, which allows more joints in a kinematic chain or a higher load for a stiffer joint. Additionally, the disclosed embodiments can achieve geared motion with maintained separation in a structure that may be more compact than is possible with pin type joints, allowing for more space for a lumen in a wrist. The compact nature of the joint allows for a cross axis (U-joint) type design in a space practical for surgical robotics. This can also reduce the overall length of a tool and/or increase the range of motion of an instrument. The U-joint arrangement also produces a symmetric workspace, which can be an advantage in a control system and surgeon training. Blending the curves together (from ID to OD) creates a joint that resists slippage and translation because of angled contact. Also, the compact size of the features allows for sets of joints to be used back to back to resist slippage and translation. U-joints made using blended or non-blended cycloidal surfaces can be made with crossing tilt axes for a compact structure or with a stacked structure providing more area for a larger central lumen.

Figure 12:
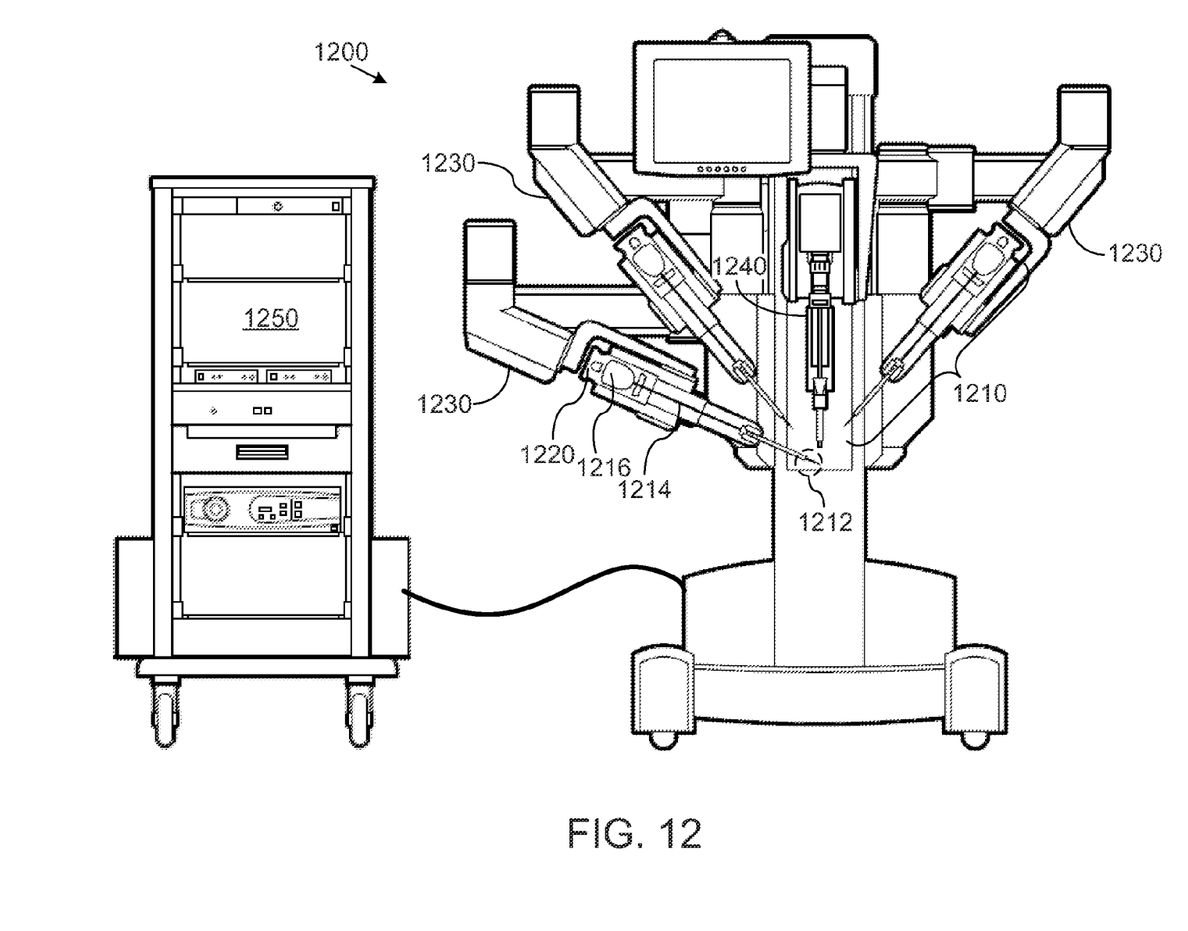
FIG. 12 shows a robotically controlled system including wrist mechanisms in minimally invasive medical instruments.

FIG. 12 shows an example of a robotically controlled system 1200 capable of using medical instruments containing wrist mechanisms such as described above. System 1200, which may, for example, be a da Vinci® Surgical System available from Intuitive Surgical, Inc. includes multiple medical instruments 1210, each of which is mounted on a docking port 1220 on a robotic manipulator arm 1230. Instruments 1210 can be made interchangeable, so that the instruments 1210 mounted in docking ports 1220 can be selected for a particular medical procedure or changed during a medical procedure to provide the clinical functions needed. Each instrument 1210 generally includes an end effector 1212, a main tube 1214, and a backend mechanism 1216 End effectors 1212 of instruments 1210 include tools such as forceps or graspers, needle drivers, scalpels, cauterizers, or scissors, and the mechanical wrist mechanisms can be incorporated into end effectors 1212 to manipulate those tools. Alternatively, the wrist mechanisms described above could be employed in a main tube 1214. In use, one or more end effector 1212 and distal portions of main tubes 1214 can be inserted through one or more small incisions or a natural orifice to position end effectors 1212 at a work site inside a patient. Docking ports 1220 generally include drive motors that provide mechanical power for manipulation of tendons that extend from backend mechanisms 1216 through main tubes 1214 and connect to wrist mechanisms and tools in instruments 1210. A computer system 1250 executes software that controls the drive motors as needed to manipulate instruments 1210 as directed by a surgeon or other medical personnel using system 1200 to perform a medical procedure.

Although the invention has been described with reference to particular embodiments, the description is only an example of the invention's application and should not be taken as a limitation. Various adaptations and combinations of features of the embodiments disclosed are within the scope of the invention as defined by the following claims.

What is claimed is:

1. An instrument wrist comprising:
   a first member having a first cycloidal surface;
   a second member having a second cycloidal surface in contact with the first cycloidal surface, wherein compressing forces on the first and second members are born by contact of the first and second cycloidal surfaces, and one of the first and second cycloidal surfaces is concave where the first and second surfaces contact; and
   a tendon connected to apply force to one of the first and second members, wherein the first and second members are arranged for geared motion in response to the force applied through the tendon.

2. The wrist of claim 1, wherein the first cycloidal surface has a portion that follows an epicycloidal curve and contacts a portion of the second cycloidal surface that follows a hypocycloidal curve.

3. The wrist of claim 2, wherein the first member further comprises a third cycloidal surface having a portion that follows a hypocycloidal curve, and the second member comprises a fourth cycloidal surface that contacts the third cycloidal surface and follows an epicycloidal curve.

4. The wrist of claim 3, wherein the first, second, third, and fourth cycloidal surfaces are arranged so that a tendency of the first and second cycloidal surfaces to slip relative to geared motion in response to the force applied to one of the first and second members is balanced by an opposing tendency the third and fourth cycloidal surfaces to slip relative to geared motion in response to the force.

5. The wrist of claim 3, wherein the first and third cycloidal surfaces are located along a diameter of the first member and are on the same side of a center of the diameter.

6. The wrist of claim 3, wherein the first and third cycloidal surfaces are located along a diameter of the first member and are on opposite sides of a center of the diameter.

7. The wrist of claim 1, wherein the first cycloidal surface smoothly transitions from a portion of a first epicycloid to a portion of a first hypocycloid.

8. The wrist of claim 7, wherein the second cycloidal surface smoothly transitions from a portion of a second hypocycloid to a portion of a second epicycloid.

9. The wrist of claim 8, wherein:
at a location where the first epicycloid contacts the second hypocycloid, the first and second members have a first tendency to slip relative to geared motion in response to the force applied to one of the first and second members;
at a location where the first hypocycloid contacts the second epicycloid, the first and second members have a second tendency to slip relative to the geared motion in response to the force; and
the second tendency opposes the first tendency.

10. The wrist of claim 7, wherein the first member further comprises a third cycloidal surface that smoothly transitions from a portion of an epicycloid to a portion of a hypocycloid, wherein the first and third surfaces are located along a diameter of the first member and are on opposite sides of a center of the diameter.

11. The wrist of claim 1, wherein:
the first member further comprises a first gear structure;
the second further comprises a second gear structure; and
when the first surface is in contact with the second surface, the first gear structure meshes with the second gear structure and provides a 1:1 ratio for rotations of the first and second members.

12. The wrist of claim 11, wherein:
the first gear structure comprises a tooth; and
the second gear structure comprises a slot in the second member.

13. The wrist of claim 1, wherein the first cycloidal surface comprises a first portion that follows an epicycloidal surface and a second portion that follows a hypocycloid.

14. The wrist of claim 1, wherein the first cycloidal surface comprises a central portion that follows one of an epicycloid and a hypocycloid and two outer portions that follow the other of a hypocycloid and an epicycloid.

15. The wrist of claim 1, wherein the first cycloid includes a central portion that is shaped as an epicycloid revolved about a center axis of the wrist.

16. The wrist of claim 15, wherein the second cycloidal surface has a central portion shaped as a hypocycloid revolved about the center axis of the wrist.

17. The wrist of claim 1, wherein:
the first cycloidal surface is a surface of a projection extending from a body of the first member; and
the second cycloidal surface is a surface of a projection extending from a body of the second member.

18. The wrist of claim 1, wherein the second member comprises a third cycloidal surface on a side of the second member opposite to the second cycloidal surface, and the wrist further comprising a third member having a fourth cycloidal surface in contact with the third cycloidal surface.

19. The wrist of claim 18, wherein:
contact of the first and second cycloidal surfaces limits motion of the first member relative to the second member to rotation about a first tilt axis; and
contact of the third and fourth cycloidal surfaces limits motion of the third member relative to the second member to rotation about the first tilt axis.

20. The wrist of claim 18, wherein:
contact of the first and second cycloidal surfaces limits motion of the first member relative to the second member to rotation about a first tilt axis; and
contact of the third and fourth cycloidal surfaces limits motion of the third member relative to the second member to rotation about a second tilt axis that is perpendicular to the first tilt axes.

21. The wrist of claim 18, wherein the second member is saddle shaped.

22. The wrist of claim 21, wherein the second and third cycloidal surfaces are positioned on the second member so as to cross the axis of motion of the wrist in the same plane.

23. The wrist of claim 18, wherein each of the first, second, third, and fourth cycloidal surfaces comprises a blended cycloidal surface.

24. The wrist of claim 18, wherein each of the first, second, third, and fourth cycloidal surfaces comprises a stepped cycloidal surface.

25. The wrist of claim 18, wherein each of the first, second, third, and fourth cycloidal surfaces is such that a plane parallel to a tilt axis of the wrist intersects the cycloidal surface along a straight line.

26. The wrist of claim 1, wherein the geared motion preserves a separation between reference points corresponding to centers of the first and second cycloidal surfaces.

27. The wrist of claim 26, further comprising a second tendon connected to amply force to one of the first and second members, wherein the force applied through the second tendon causes geared motion of the first and second members in a direction opposite to the geared motion caused by the force applied through the first tendon.

* * * * *